US006659307B1

United States Patent
Stradella

(10) Patent No.: US 6,659,307 B1
(45) Date of Patent: Dec. 9, 2003

(54) DOSE COUNTER AND DISTRIBUTOR OF A FLUID PRODUCT INCORPORATING A COUNTER OF THIS TYPE

(75) Inventor: Giuseppe Stradella, Camogli (IT)

(73) Assignee: Valois S.A.S., Le Neubourg (FR)

( * ) Notice: Subject to any disclaimer, the term of this patent is extended or adjusted under 35 U.S.C. 154(b) by 0 days.

(21) Appl. No.: 10/110,943
(22) PCT Filed: Oct. 12, 2000
(86) PCT No.: PCT/FR00/02845
    § 371 (c)(1),
    (2), (4) Date: Sep. 25, 2002
(87) PCT Pub. No.: WO01/29765
    PCT Pub. Date: Apr. 26, 2001

(30) Foreign Application Priority Data

Oct. 19, 1999 (FR) .............................. 93 13001

(51) Int. Cl.⁷ ................................ B67D 5/06
(52) U.S. Cl. ............................ 222/23; 222/37; 116/278
(58) Field of Search ..................... 222/23, 37; 116/278

(56) References Cited

U.S. PATENT DOCUMENTS

| | | | | |
|---|---|---|---|---|
| 3,355,067 A | * | 11/1967 | Espinal .................... | 222/23 |
| 4,817,822 A | * | 4/1989 | Rand et al. .................... | 222/38 |
| 5,482,030 A | * | 1/1996 | Klein ...................... | 128/200.23 |
| 5,799,651 A | * | 9/1998 | Garby et al. ............ | 128/200.23 |
| 5,988,496 A | * | 11/1999 | Bruna ........................ | 235/91 R |
| 6,076,521 A | * | 6/2000 | Lindahl et al. ......... | 128/203.15 |
| 6,164,494 A | * | 12/2000 | Marelli ........................ | 222/38 |
| 6,283,365 B1 | * | 9/2001 | Bason .................... | 235/116 |
| 6,336,453 B1 | * | 1/2002 | Scarrott et al. .......... | 128/200.23 |

* cited by examiner

Primary Examiner—Gene Mancene
Assistant Examiner—Melvin A Cartagena
(74) Attorney, Agent, or Firm—Sughrue Mion, PLLC

(57) ABSTRACT

A dose counter device for a fluid dispenser, said device comprising counting means (10, 11) actuated by actuating means (20) each time the dispenser is used, said device being characterized in that said counting means comprise at least one flexible rotary counting element (10) applied against and turning on a curved support surface (1, 2).

18 Claims, 5 Drawing Sheets

DOSE COUNTER AND DISTRIBUTOR OF A FLUID PRODUCT INCORPORATING A COUNTER OF THIS TYPE

The present invention relates to a dose counter device and to a fluid dispenser incorporating such a dose counter.

Dose counter systems for fluid dispenser devices are well known in the state of the art. Such a dose counter system generally comprises counting means that are usually in the form of rotary disks, and that are turned through a predetermined angle each time the fluid dispenser is actuated. Such disks generally carry digits to indicate the number of metered quantities or "doses" dispensed or remaining to be dispensed, the digits generally being provided on the outer peripheral edges of such counting disks, i.e. on the outer edge that defines the thickness of the counting disk. Thus, each time the fluid dispenser is actuated, a corresponding digit comes into register with a suitable window enabling said digit to be viewed from outside the dispenser. Counters of this type are disclosed in particular in Documents EP-0 484 188, EP-0 472 915, EP-0 539 469, EP-0 539 469, EP-0 764 312, and WO 98/01822.

Those counters suffer from drawbacks. Firstly, the presence of such a counter in a fluid dispenser device implies that the size of said dispenser device must be increased, and the larger the number of doses to be counted, the larger the volume required for the counter system. In particular, in order to count a large number of doses, it is necessary either to increase the diameter of the counting disk so that it is possible to write more digits on the edge of the disk, or else to provide one or more superposed counting disks co-operating, for example, by means of a cam system, the disks then representing respectively the units, the tens, the hundreds, etc. The size of the counter system is then increased considerably along the axis of rotation of said counting disks. In addition, such dose counter systems are not easy to adapt to a dispenser device, and relatively complex means for actuating the counter are generally necessary for coupling actuating of the counter to actuating of the fluid dispenser device. Furthermore, that type of counter is not generally adaptable to dispenser devices that have various different actuating strokes. Thus, for example, in a metering valve, the actuating stroke of the valve member can vary depending on the metering valve model used, so that specific actuating means must be provided for each valve model. In addition, the actuating stroke of the valve member of a single metering valve can vary between succession occasions on which said valve is actuated, which can give rise to malfunctioning in the counting of the doses, it being possible that a dose might not be counted, or might be counted twice due to the variable actuating stroke being respectively too short or too long.

An object of the present invention is to provide a dose counter device for a fluid dispenser that does not suffer from the above-mentioned drawbacks.

In particular, an object of the present invention is to provide a dose counter device that is simple and inexpensive to manufacture and to assemble.

An object of the present invention is also to provide such a dose counter device that does not significantly change the outside dimensions of the fluid dispenser device to which it is applied.

An object of the present invention is also to provide such a dose counter device that is capable of counting any number of doses, including very large numbers, without significantly changing the size of the fluid dispenser.

A further object of the present invention is to provide such a dose counter device that can be used with actuating members, in particular valves, that have variable actuating strokes.

The present invention thus provides a dose counter device for a fluid dispenser, said device comprising counting means actuated by actuating means each time the dispenser is used, said device being characterized in that said counting means comprise at least one flexible rotary counting element applied against and turning on a curved support surface.

Preferably, said flexible counting element is deformed each time it is actuated so as to remain in contact with said curved support surface.

Advantageously, said flexible counting element is in the form of a disk, and is provided with a ring of serrations or the like around its outer edge, which ring of serrations is suitable for co-operating with said actuating means.

In a particular embodiment of the present invention, said counting means comprise two superposed flexible rotary counting elements, said actuating means co-operating with the first counting element, and coupling means being provided between the two counting elements for causing the second counting element to turn, said coupling means being mounted to move between a non-coupling position and a coupling position.

Advantageously, said counting elements turn about a common axis of rotation, said coupling means comprising a resilient tab secured to or integral with one of the two counting elements and co-operating with a slot provided in the other counting element, said tab being urged into the coupling position by cam means each time the first coupling element has turned through one full turn.

In a variant, said counting elements turn about mutually offset parallel axes of rotation, said coupling means comprising a stud that is secured to or integral with one of the two counting elements, that co-operates with a projection secured to or integral with the other counting element, and that comes into the coupling position each time the first counting element turns through one full turn.

Advantageously, the second counting element is implemented in the form of a flexible disk or of an angular sector of flexible disk.

Advantageously, one of the two superposed flexible counting elements is provided with a window for viewing the other counting element.

Advantageously, one of the two superposed flexible counting elements is organized to be transparent for the purpose of viewing the other counting element.

The present invention also provides a dispenser for dispensing a fluid, said dispenser comprising a fluid reservoir, a dispensing member, such as a pump or a valve, and a dispensing orifice, for selectively dispensing said fluid, said dispenser further comprising a dose counter disk.

Preferably, said at least one counting element is disposed between two concentric substantially cylindrical surfaces, the axis of rotation of said at least one counting element being substantially perpendicular to said substantially cylindrical surfaces.

Advantageously, said at least one counting element is disposed between the outer body of the dispenser and an inner body inside which the reservoir is mounted.

In a first embodiment of the invention, said reservoir is mounted to slide inside said inner body, said reservoir co-operating with said actuating means for actuating the dose counter device, so that, by moving, the reservoir causes the counter to be actuated.

Advantageously, said actuating means comprise an actuating finger mounted to be moved with the reservoir so as to co-operate with said counting element, said finger being flexible, at least in the direction in which the reservoir moves, so that it can adapt to accommodate various displacement strokes over which the reservoir is moved.

Advantageously, the dispensing member is a metering valve adapted to dispensing a fluid with a propellant gas, the displacement stroke of the reservoir corresponding to the actuating stroke of the valve member of the metering valve.

Advantageously, said flexible finger is part of an actuator member mounted to slide between said inner body of the dispenser and said reservoir, said inner body defining a window through which said flexible finger co-operates with said counting element, said window being provided with an abutment against which said flexible finger comes when it moves axially, so that any additional axial movement causes said flexible finger to be deformed elastically.

In a second embodiment of the present invention, the reservoir is mounted to be fixed in the body of the dispenser, said dispenser further comprising a dispensing element for actuating said dispensing member, said actuating means for actuating said dose counter device being constrained to move with said dispensing element.

Advantageously, said dispensing element is a cover mounted to pivot between a position in which the dispensing orifice is closed, and a dispensing position, the dispensing member being a pump triggerable by inhaling.

Other characteristics and advantages of the present invention will appear on reading the following detailed description of two particular embodiments of the present invention given by way of non-limiting example with reference to the accompanying drawings, in which.

Figure 1:
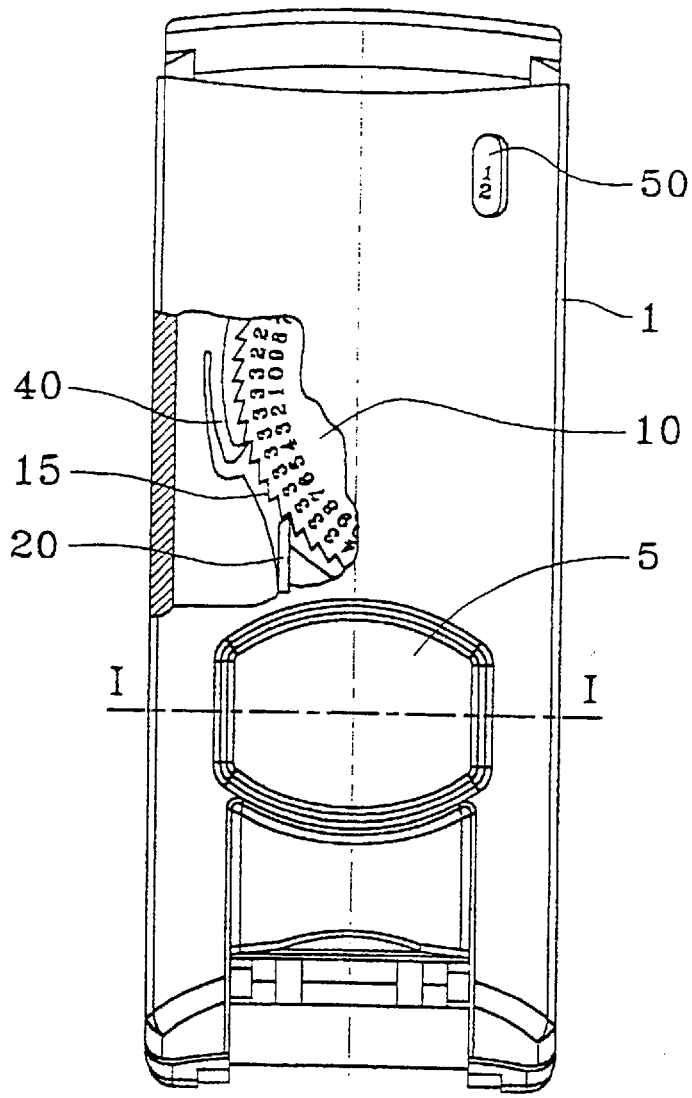
FIG. 1 is a diagrammatic partially cut-away section view of a fluid dispenser incorporating a dose counter device of the present invention.

The dose counting dispenser of the present invention includes one or more flexible rotary counting elements. Advantageously, the counting element is implemented in the form of a flexible disk 10 which is applied against a curved and in particular substantially cylindrical support surface. The flexible disk 10 may be applied against a convex surface or against a concave surface depending on whether it is placed on the inside or on the outside of said support surface. However, in the description below, and in the preferred embodiments, the counting disk 10 is advantageously disposed between two concentric surfaces which define a small gap between them, in which said flexible disk 10 is disposed. Advantageously, these two surfaces are constituted by the outer body 1 of the fluid dispenser device, and an inner body 2 fixed to said outer body 1.

The or each counting element 10 advantageously turns about an axis of rotation that is substantially perpendicular to said curved support surface(s). As described in more detail below, when two or more disks are provided, they can turn either about a common axis of rotation 60, or else about respective mutually offset axes of rotation 60, 61.

The flexible counting disk 10 co-operates with actuating means 20, and the outer periphery of the counting disk 10 is advantageously provided with a ring of serrations 15 or the like. The actuating means 20 successively come into engagement with a respective serration of said ring of serrations 15 each time said fluid dispenser device is actuated. Advantageously, said actuating means comprise an actuating finger 20. The actuating finger 20 is preferably flexible as described in more detail below. It is also possible to provide non-return means 40 for preventing the counting disks from turning in a direction opposite from the direction of the turning imparted by said actuating means 20. The non-return means may comprise a flexible catch 40 co-operating with said ring of serrations 15 in known manner.

Figure 6:
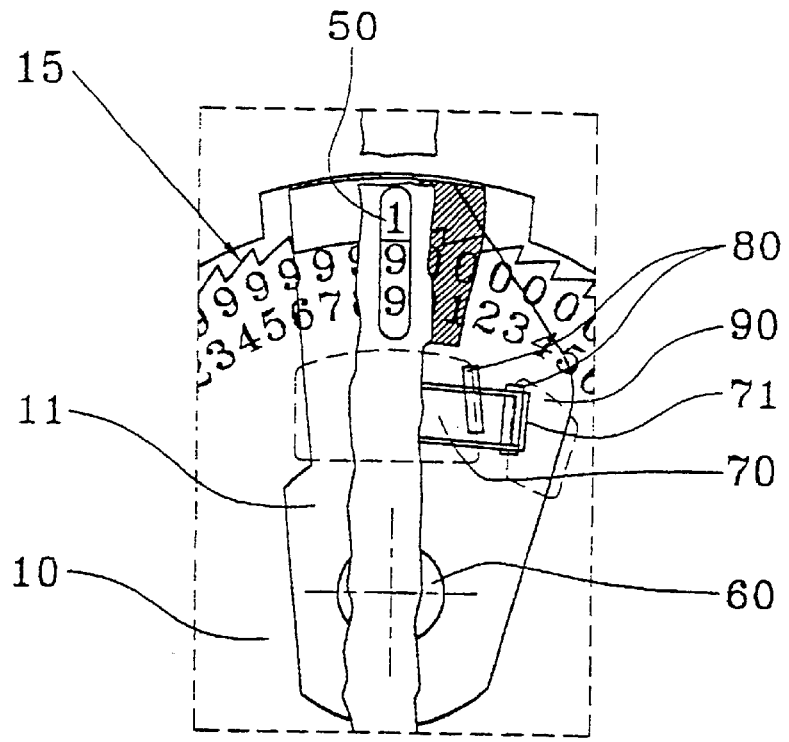
FIGS. 6 and 7 are diagrammatic views of a dose counter device comprising two superposed counting elements, in a first variant embodiment of the present invention.
Figure 7:
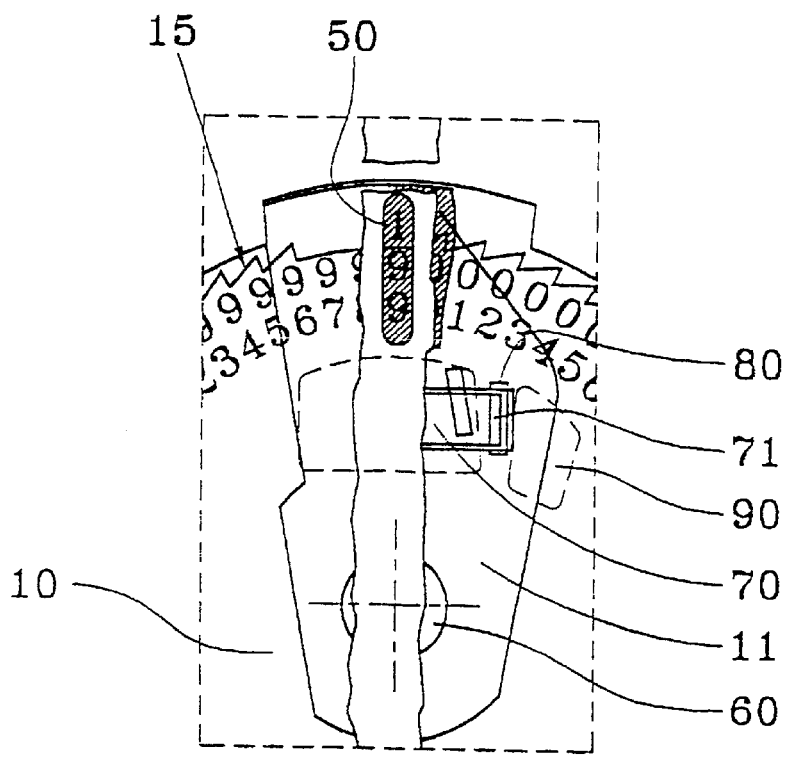

FIGS. 6 to 9 show two variant embodiments of a dose counter device comprising two superposed counting elements 10 and 11. The first embodiment, shown in FIGS. 6 and 7, shows a first counting element 10 implemented in the form of a flexible disk whose outer peripheral edge is provided with a ring of serrations 15 co-operating with actuating means 20 (not shown in the figures). Each serration of the ring of serrations 15 corresponds to a digit. In the example shown, the digits range from 0 to 99, i.e. the ring of serrations 15 comprises 100 serrations. Said first flexible disk 10 turns about an axis perpendicular to the central longitudinal axis of the curved surface against which said flexible counting disk 10 is applied. A second flexible rotary counting element 11 is superposed on the first counting disk 10, and, in the example shown, is constituted by a sector of a disk. It could also be implemented in the form of a full disk, depending on the desired amounts to be indicated. The two counting elements, namely the first flexible disk 10 and the superposed flexible sector of a disk 11, turn about a common axis of rotation 60, and coupling means 70, 80 are provided between the two counting elements 10 and 11 so as to couple the two counting elements together in predetermined manner, so that the first flexible counting disk 10 turning causes the superposed flexible sector of a disk 11 to turn simultaneously. The coupling means may advantageously comprise a flexible tab 70 whose end is provided with a projection 71 forming a sort of hook. The second counting element (the sector of a disk 11, in this example) is provided with a plurality of slots 80 positioned so as to receive said projection 71 when the two counting disks are to be coupled together. Cam means 90 are provided to urge the flexible tab 70 and to deform it so that the projection 71 penetrates into the slot, thereby securing the two counting elements 10 and 11 together. The coupling is preferably achieved each time the first counting disk 10 turns through one full turn. Said cam means 90 may be formed in particular by a protuberance or the like provided in the support surface against which the first counting disk 10 is applied. Naturally, any equivalent means making it possible to urge the flexible tab 70 of the first counting disk 10 into the slot 80 of the second counting disk 11 may be considered. Similarly, said coupling means 70 and 80 may be made in a different manner. In particular, the coupling means could be inverted, i.e. it would be the second counting element 11 that supports the resilient coupling means 70, while the first coupling disk 10 incorporates the slot(s) 80.

Figure 8:
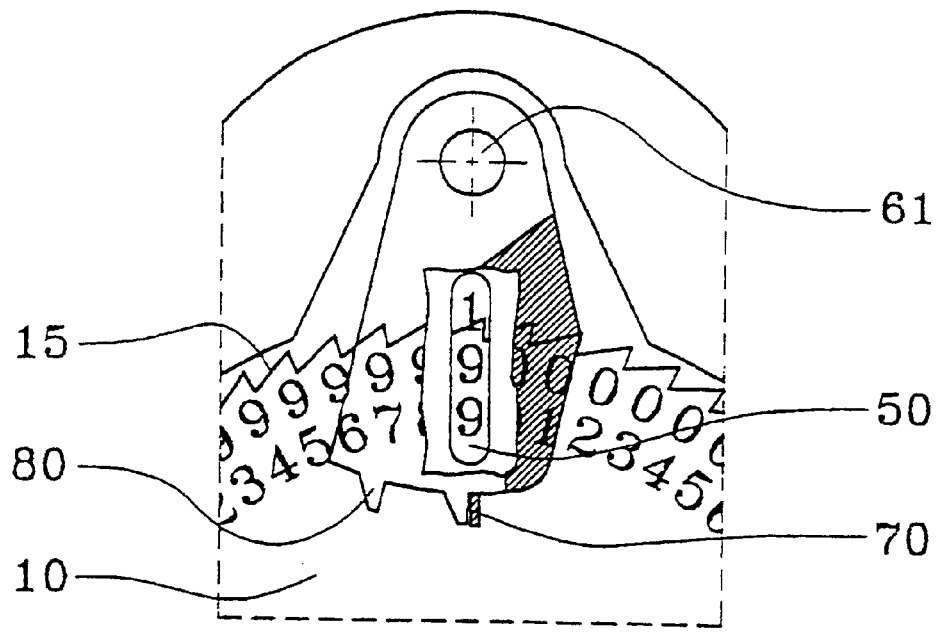
FIGS. 8 and 9 are diagrammatic views of a dose counter device comprising two superposed counting elements in a second variant embodiment of the present invention.
Figure 9:
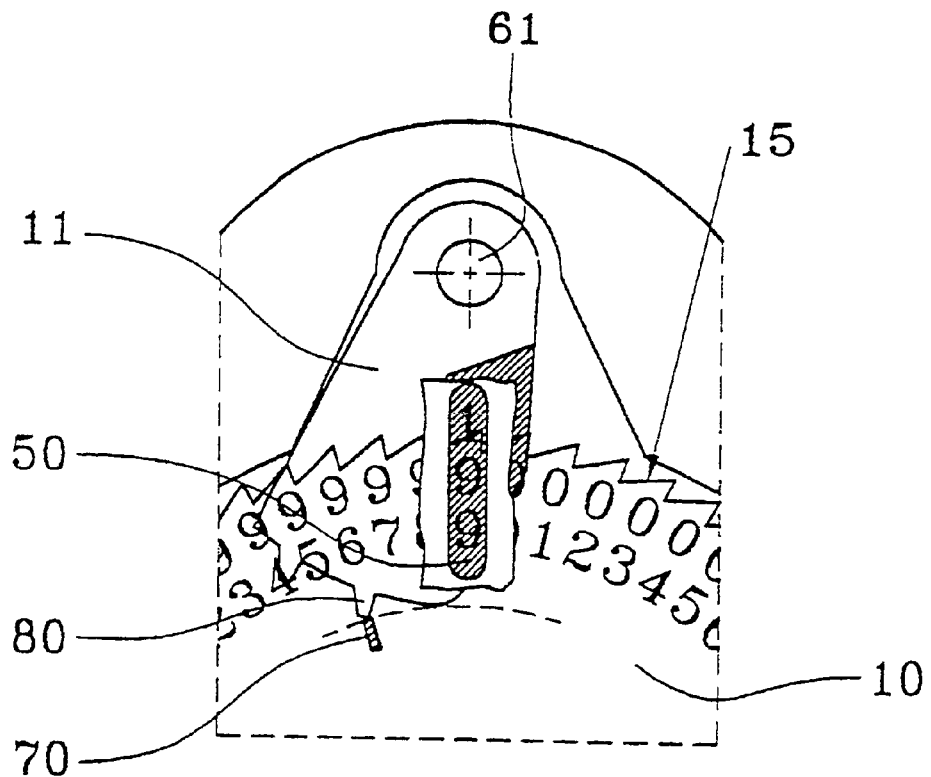

FIGS. 8 and 9 show a second variant embodiment, in which the two rotary counting elements turn about respective axes of rotation 60 and 61 that are different. Once again, in this example, the second counting element 11 is implemented in the form of a sector of a disk, but it may also be implemented in the form of a full disk, if desired. In this example, the coupling means comprise a stud 70 secured to or integral with the first counting element and which is suitable for co-operating with projections 80 provided on the second counting element 11. Each time the first counting element turns through one full turn, said stud 70 comes to drive a projection 80 on the second counting element 11, thereby coupling together said two counting elements. Any other variant of the coupling means may also be considered in this example.

In the two embodiments described above with reference to FIGS. 6 to 9, the second counting element 11 is advantageously disposed on the first counting element 10, in the direction in which the user views it, i.e. the second counting element 11 is interposed between the first counting element 10 and a viewing window 50 provided in the outer body 1 of the fluid dispenser device. In which case, the numerals or indications on the second counting element are advantageously printed on a transparent surface, so that said second counting element 11 does not mask the numerals or indications on the first counting element 10, disposed below. Optionally, it is also possible to provide a viewing window making it possible to see the digits written on the counting element 10 disposed below.

Advantageously, the second counting element 11 has a blacked-out portion which comes into register with the viewing window 50 of the fluid dispenser device after the last dose of fluid has been dispensed. This makes it possible to predetermine a theoretical number of maximum doses to be dispensed by the fluid dispenser, so that, after the last theoretical dose has been dispensed, the viewing window is blacked out, and the user is aware that the device must no longer be used. However, the device is not prevented from being actuated, and it is possible to continue to actuate the fluid dispenser device, without any indication being displayed in the viewing window 50.

The dose counter device of the present invention is applicable to any type of fluid dispenser device, and the following detailed description is made with reference to two particular embodiments, in which the dose counter is applied firstly to an inhaler-type device that is actuated by inhaling and that is referred to as a Breath-Actuated Inhaler (BAI), and secondly to a device of the aerosol inhaler type that is referred to as a Metered Dose Inhaler (MDI). Naturally, the present invention is not limited to these two examples.

Figure 2:
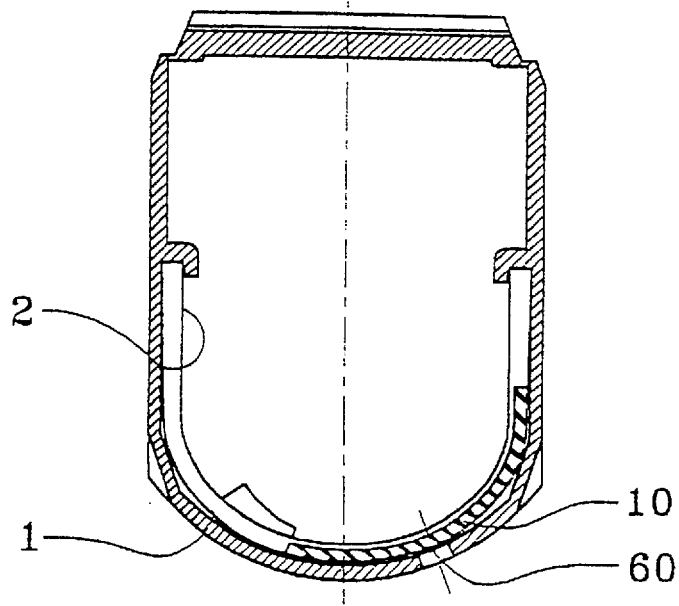
FIG. 2 is a diagrammatic horizontal section view on line I—I of the device shown in FIG. 1.

FIGS. 1 and 2 show an inhaler, in particular an inhaler triggered by the patient inhaling. The device includes an outer body 1 provided with a viewing window 50. The counting element 10 is applied inside said outer body 1 and against an inner body 2 forming a curved support surface. As shown in FIG. 2, the curved surface is not necessarily cylindrical, the flexibility of the counting element 10 enabling it to turn about its axis of rotation 60 while remaining continuously in contact with the two curved surfaces that flank it, i.e. the outer body and the inner body 1 and 2 of the dispenser, independently of the shapes of said curved surfaces. The actuating means comprise an actuating finger 20 that is mounted to be displaced axially, and whose end co-operates with the peripheral ring of serrations on the outer element 10. Advantageously, said actuating finger 20 is secured to or integral with a pusher, or to some other dispensing element of this type. In particular, the actuating finger 20 may be secured to or integral with a cover mounted to move between a closed position in which it closes the dispensing orifice 5 and a dispensing position, the cover being mounted to pivot on the outer body of the dispenser, the cover pivoting causing the actuating finger 20 to travel over its axial stroke, thereby causing the counting element 10 to turn.

Figure 3:
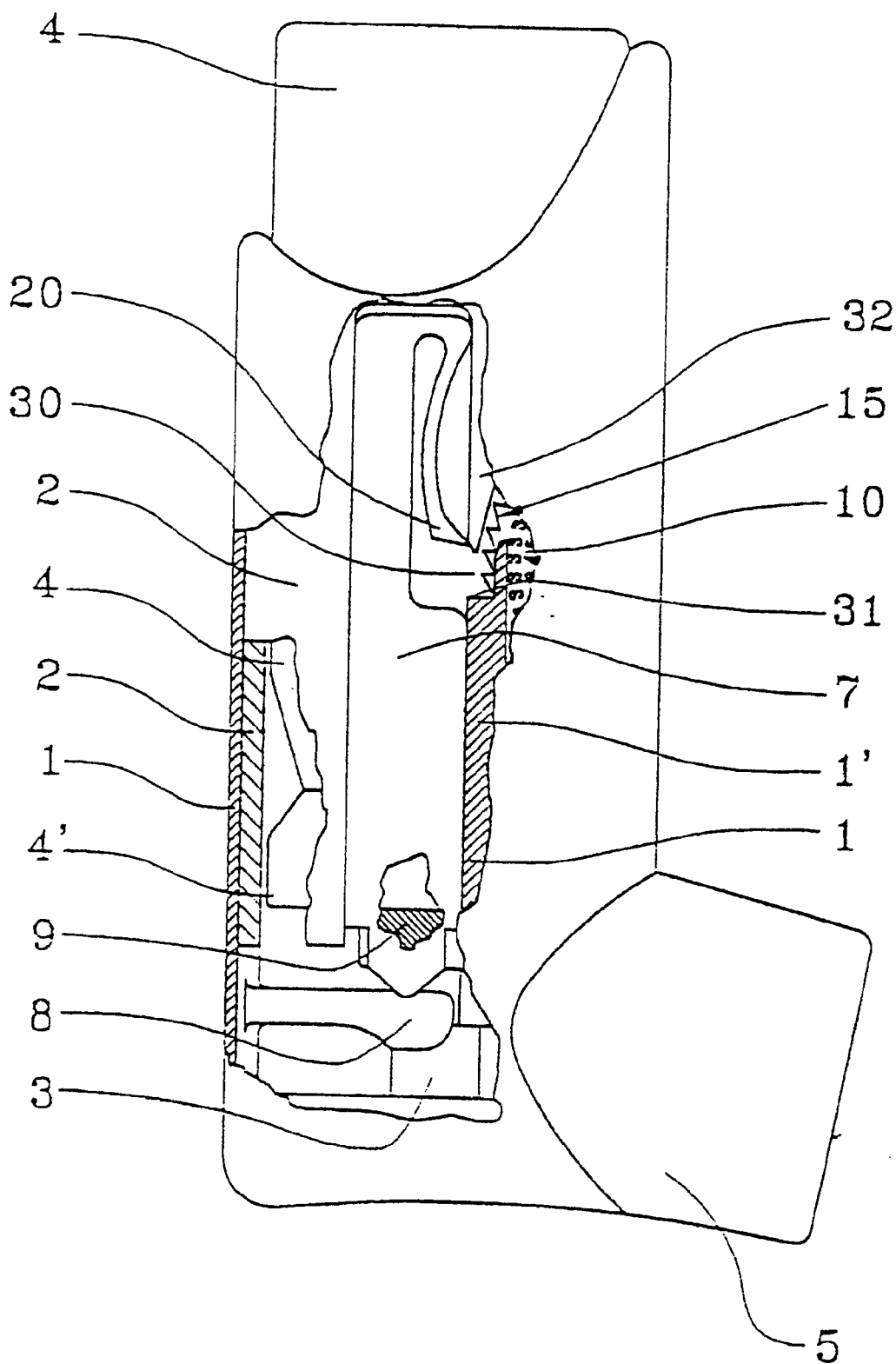
FIG. 3 is a diagrammatic partially cut-away section view of a fluid dispenser incorporating a second embodiment of a dose counter device of the present invention.
Figure 4:
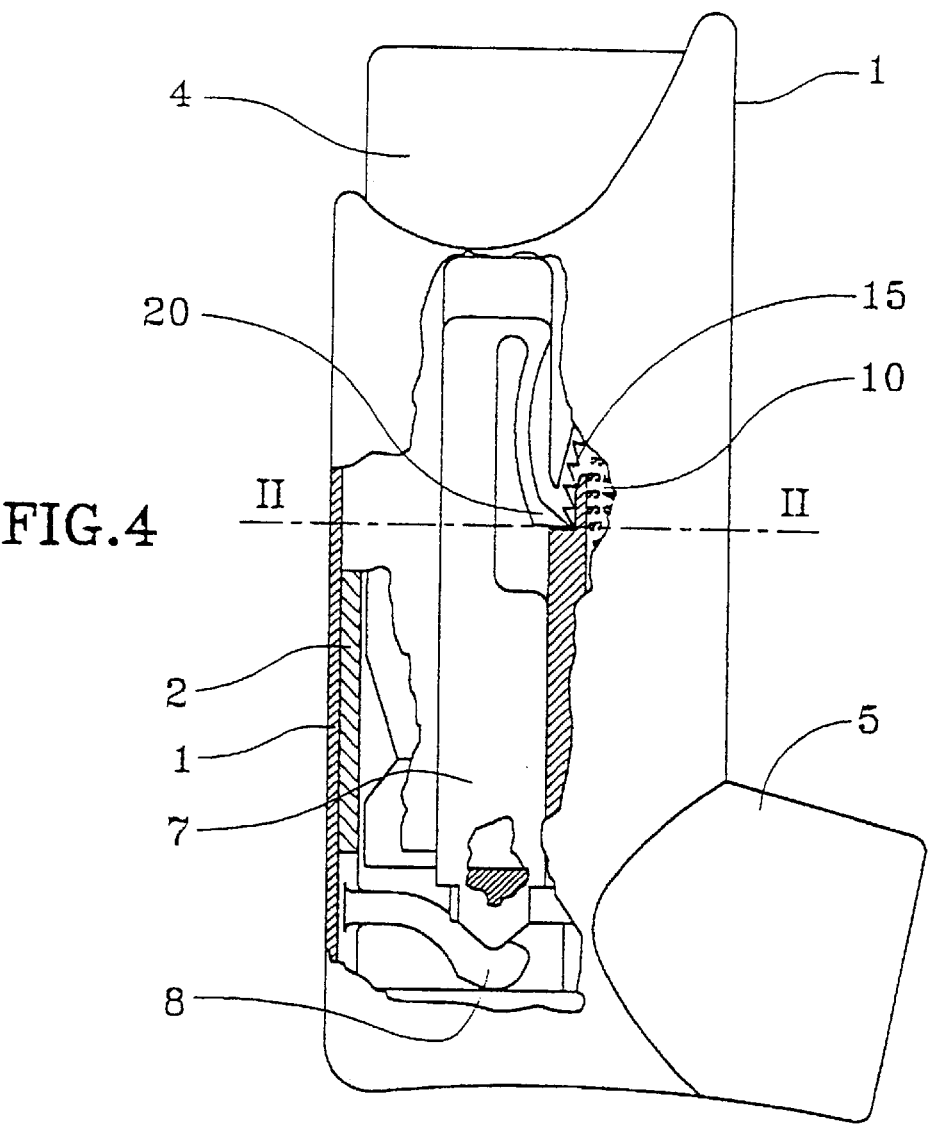
FIG. 4 is a view similar to the view in FIG. 3, with the fluid dispenser in the actuated position.
Figure 5:
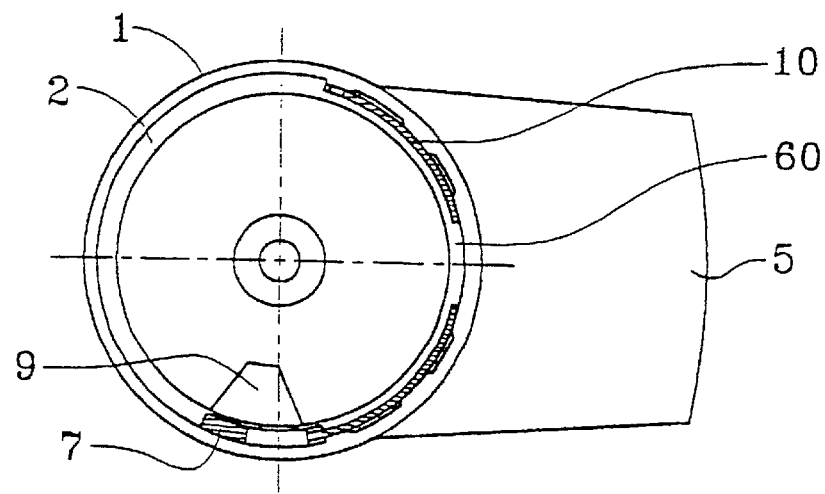
FIG. 5 is a diagrammatic horizontal section view on line I—I of the device of FIG. 4.

FIGS. 3 to 5 show a second embodiment, applied to an MDI. This type of device generally has an outer body 1 incorporating a mouthpiece provided with the dispensing orifice 5. The fluid reservoir 4, containing the fluid dispersed in a propellant gas, is mounted to slide inside said outer body 1, and is provided with a metering valve. The reservoir 4 moving thus causes the valve member of the metering valve 3 (not shown in detail) to move, thereby expelling a dose of fluid. An inner body 2 is mounted inside the outer body 1, the counting element 10 being provided between the inner body 2 and the outer body 1. Advantageously, the reservoir 4 is cylindrical, as are the inner body and the outer body, so that the counting element 10 is applied against a cylindrical surface. The present invention is however also applicable to curved support surfaces that are not cylindrical. An actuator member 7 is mounted to slide between the inner body 2 and the reservoir 4, said actuating member 7 incorporating a flexible actuating finger 20 whose end serves to co-operate with the peripheral ring of serrations 15 on the counting element 10. The actuator member 7 is mounted to move axially against a resilient element 8, such as a flexible tab or a spring, suitable for returning said actuator member 7 into the starting position, after a full actuating cycle. The actuator member 7 further advantageously includes a control shoulder 9 which presses against the neck 4' of the reservoir 4 containing the fluid. The actuator 7, which slides inside the inner body 2, is advantageously mounted to slide on a support seat formed in part by the inner body 2 and completed by a rib 1' formed in the outer body 1. A side wall 32 of said seat and said rib 1' define an opening or a window 30 through which the end of the flexible finger 20 can penetrate to co-operate with the counting member 10. Advantageously, the rib 1' is provided with a shoulder 31 which forms an abutment against which the flexible actuating finger 20 comes when it moves axially.

The system shown in FIGS. 3 to 5 operates as follows. When the fluid dispenser device is actuated, the reservoir 4 is moved vertically downwards, as shown in FIGS. 3 and 4. Under the effect of the control shoulder 9, the actuator member 7 slides with said reservoir 4. Thus, the tip of the resilient actuating finger 20 penetrates into the window 30 and co-operates with a serration on the flexible counting element 10, thereby causing it to turn. The angle of rotation through which the counting element 10 turns is determined and limited by the position of the shoulder 31, so that said angle of rotation is independent of the length of the actuating stroke of the reservoir 4. If the actuating stroke of the reservoir 4 is longer, the tip of the flexible finger 20 is stopped by the abutment shoulder 31, and any additional axial displacement is absorbed by said flexible finger 20 flexing. Advantageously, said finger is flexible both horizontally and vertically. Similarly, while the actuator member 7 is returning to its rest position, under the effect of the resilient element 8, the tip of the actuating finger 20 exits from the window 30, still in the same position because of the presence of the side wall 32, and any additional vertical movement is absorbed by said flexible finger 20 flexing horizontally. Since the actuating stroke of said reservoir 4 corresponds to the actuating stroke of the metering valve 3 mounted on said reservoir, the counter system of the present invention is thus applicable to different valves having different actuating strokes. It also makes it possible for the doses dispensed by a metering valve having actuating strokes that vary between successive occasions on which it is actuated to be counted reliably.

Depending on the positioning of the window 30 defined between the shoulder 31 of the rib 1' and the side wall 32 of the seat of the actuator member 7, the counting element 10 is turned at the beginning of the actuating stroke of the reservoir 4, at the end of said stroke, or between the two ends.

Naturally, various modifications may be considered without going beyond the ambit of the present invention, whose scope is defined by the accompanying claims.

What is claimed is:

1. A dose counter device for a fluid dispenser, said device comprising counting means (10, 11) actuated by actuating means (20) each time the dispenser is used, said device being characterized in that said counting means comprise at least one flexible rotary counting element (10) applied against and turning on a curved support surface (1, 2).

2. A device according to claim 1, in which said flexible counting element (10) is deformed each time it is actuated so as to remain in contact with said curved support surface (1, 2).

3. A device according to claim 1, in which said flexible counting element (10) is in the form of a disk, and is provided with a ring of serrations (15) or the like around its outer edge, which ring of serrations is suitable for co-operating with said actuating means (20).

4. A device according to claim 1, in which said counting means comprise two superposed flexible rotary counting elements (10, 11), said actuating means (20) co-operating with the first counting element (10), and coupling means (70, 80) being provided between the two counting elements (10, 11) for causing the second counting element (11) to turn, said coupling means (70, 80) being mounted to move between a non-coupling position and a coupling position.

5. A device according to claim 4, in which said counting elements (10, 11) turn about a common axis of rotation (60), said coupling means comprising a resilient tab (70) secured to or integral with one of the two counting elements (10, 11) and co-operating with a slot (80) provided in the other counting element (11, 10), said tab (70) being urged into the coupling position by cam means (90) each time the first coupling element (10) has turned through one full turn.

6. A device according to claim 4, in which said counting elements (10, 11) turn about mutually offset parallel axes of rotation (60, 61), said coupling means comprising a stud (70) that is secured to or integral with one of the two counting elements (10, 11), that co-operates with a projection (80) secured to or integral with the other counting element (11, 10), and that comes into the coupling position each time the first counting element (10) turns through one full turn.

7. A device according to claim 4, in which the second counting element (11) is implemented in the form of a flexible disk or of an angular segment of flexible disk.

8. A device according to claim 4, in which one of the two superposed flexible counting elements (10, 11) is provided with a window (100) for viewing the other counting element (11, 10) in part.

9. A device according to claim 4, in which one of the two superposed flexible counting elements (10, 11) is organized to be transparent for the purpose of viewing the other counting element (11, 10).

10. A dispenser for dispensing a fluid, said dispenser comprising a fluid reservoir, a dispensing member (3), such as a pump or a valve, and a dispensing orifice (5), for selectively dispensing said fluid, said dispenser being characterized in that it further comprises a dose counter device according claim 1.

11. A dispenser according to claim 10, in which said at least one counting element (10) is disposed between two concentric substantially cylindrical surfaces (1, 2), the axis of rotation (60) of said at least one counting element (10) being substantially perpendicular to said substantially cylindrical surfaces (1, 2).

12. A dispenser according to claim 10, in which said at least one counting element (10) is disposed between the outer body (1) of the dispenser and an inner body (2) inside which the reservoir (4) is mounted.

13. A dispenser according to claim 12, in which said reservoir (4) is mounted to slide inside said inner body (2), said reservoir (4) co-operating with said actuating means (20) for actuating the dose counter device, so that, by moving, the reservoir (4) causes the counter to be actuated.

14. A dispenser according to claim 13, in which said actuating means (20) comprise an actuating finger (20) mounted to be moved with the reservoir (4) so as to co-operate with said counting element (10), said finger (20) being flexible, at least in the direction in which the reservoir (4) moves, so that it can adapt to accommodate various displacement strokes over which the reservoir is moved.

15. A dispenser according to claim 14, in which the dispensing member (3) is a metering valve adapted to dispensing a fluid with a propellant gas, the displacement stroke of the reservoir (4) corresponding to the actuating stroke of the valve member of the metering valve (3).

16. A dispenser according to claim 15, in which said flexible finger (20) is part of an actuator member (7) mounted to slide between said inner body (2) of the dispenser and said reservoir (4), said inner body (2) defining a window (30) through which said flexible finger (20) co-operates with said counting element (10), said window (30) being provided with an abutment (31) against which said flexible finger (20) comes when it moves axially, so that any additional axial movement causes said flexible finger (20) to be deformed elastically.

17. A dispenser according to claim 10, in which the reservoir (4) is mounted to be fixed in the body (1) of the dispenser, said dispenser further comprising a dispensing element for actuating said dispensing member, said actuating means (20) for actuating said dose counter device being constrained to move with said dispensing element.

18. A dispenser according to claim 17, in which said dispensing element is a cover mounted to pivot between a position in which the dispensing orifice (5) is closed, and a dispensing position, the dispensing member (3) being a pump triggerable by inhaling.

* * * * *